United States Patent
Buchecker et al.

[11] Patent Number: 5,851,425
[45] Date of Patent: Dec. 22, 1998

[54] IMIDAZOTHIAZOLES

[75] Inventors: Richard Buchecker, Zürich, Switzerland; Willy Friedrichsen, Wankendorf, Germany; Jürg Fünfschilling, Basel, Switzerland; Sandra Lüpfert, Kiel, Germany

[73] Assignee: Rolic AG, Zug, Switzerland

[21] Appl. No.: 824,375

[22] Filed: Mar. 26, 1997

[30]  Foreign Application Priority Data

Apr. 4, 1996 [CH] Switzerland .............................. 0887/96

[51] Int. Cl.[6] .......................... C09K 19/34; C09K 19/32; C09K 19/12; C07D 515/02

[52] U.S. Cl. ................................. 252/299.61; 252/299.62; 252/299.63; 252/299.66; 252/299.67; 548/153; 548/154; 549/455; 549/369

[58] Field of Search ........................ 252/299.61, 299.62, 252/299.01, 299.66, 299.63; 548/153, 154; 549/455, 369

[56]  References Cited

FOREIGN PATENT DOCUMENTS

| | | |
|---|---|---|
| 0144013 | 11/1984 | European Pat. Off. . |
| 463212 | 9/1992 | European Pat. Off. . |
| 3734332 | 7/1988 | Germany . |
| 178289 | 7/1990 | Japan . |
| 1070139 | 5/1967 | United Kingdom . |
| 1403841 | 8/1975 | United Kingdom . |
| 2211186 | 6/1989 | United Kingdom . |

OTHER PUBLICATIONS

ANdreani et al., Euro. J. Med Chem. 19 (3), pp. 219–222, 1984.

J. Chem, Soc., Perkin Trans. 1 (4) 856–60, 1991.

"Synthesis and Mutagenic Activity of Imidazo [2,11–b] Thiazoles Bearing At Least One Nitro Or Nitroso Group", Arch. Pharm., Chem., Sci. Ed. 1987.

"Synthesis and Mesomorphic Properties of 2, 5–Di–(4–N–Alkyloxphenyl) Thiazole[5,4–D] Thiazoles", Mol. Cryst. Liq. Cryst. 1990, vol. 180B.

"Substituted 6–Phenylimidazo[2,1–B] Thiazoles and Thiazolines as Potential Cardiotonic Agents" Eur. J. Med. Chem. Chim. Ther., 1984–19.

Primary Examiner—C. H. Kelly
Attorney, Agent, or Firm—Anderson, Kill & Olick, P. C.

[57]  ABSTRACT

Compounds of the general formula

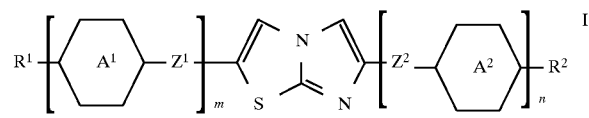

have a pronounced tendency to form liquid crystalline S (smectic) phases. Thus, optically inactive compounds of the formula I also have a tilted smectic phase, in particular an $S_C$ phase, in addition to a nematic phase. In contrast, many optically active compounds of the formula I additionally have, inter alia, a tilted smectic chiral phase, in particular a chiral $S_C$ phase, in addition to a cholesteric phase. The stated compounds are therefore particularly suitable as components and as dopants, respectively, for the preparation of a very wide range of liquid crystalline mixtures. The class of compounds comprising compounds of the general formula I offers a broad range of novel components and mixtures for optimization and modification of liquid crystalline mixtures.

15 Claims, No Drawings

IMIDAZOTHIAZOLES

BACKGROUND OF THE INVENTION

1. Field of the Invention

The present invention relates to novel imidazothiazole derivatives, liquid crystalline mixtures which contain such compounds and the use of such compounds and mixtures for optical and electro-optical apparatuses.

Liquid crystals are used in particular as dielectrics in electro-optical apparatuses, such as, for example, display apparatuses, since the optical properties of such substances can be influenced by an applied voltage. Electro-optical apparatuses based on liquid crystals are very well known to a person skilled in the art. The principle of operation of such apparatuses may be based on various effects. Thus, these apparatuses have, for example, cells with dynamic scatter, DAP cells (deformation of oriented phases), guest/host cells, TN cells having a twisted nematic structure, STN cells (super twisted nematic), SBE cells (super birefringence effect), OMI cells (optical mode interference) or TFT cells (thin film transistor).

2. Description of the Prior Art

In addition to the abovementioned cell types, whose properties are based on the use of nematic or cholesteric liquid crystals, display apparatuses which are based on the principle of tilted smectic phases, in particular chiral phases, have recently become known. Suitable tilted smectic phases are, for example, smectic C, F, G, H, I and K phases, which are referred to below as $S_C$, SF, etc. In general, $S_C$ phases which permit particularly high response speeds are preferred. The chiral tilted phases are usually denoted by $S_C^*$ $S_F^*$, etc., the asterisk indicating the chirality in each base. Known cell types which are based on the principle of chiral $S_C^*$ phases are, for example, SSF cells (surface stabilized ferroelectric), SBF cells (short-pitch bistable ferroelectric) or DHF cells (deformed helix ferroelectric).

The liquid crystal materials must have good chemical and thermal resistance and high stability to electric and magnetic fields. Furthermore, they should have a suitable mesophase over a broad temperature range, a low viscosity and short response times. Materials based on chiral tilted smectic phases should moreover have a sufficiently high spontaneous polarization and, depending on the cell type, a fairly small twisting capacity (SSF cells) or as high a twisting capacity as possible (SBF and DHF cells). In order to facilitate the orientation in the cell, these may furthermore preferably have an $S_A$ phase above the $S_C$ phase.

Suitable ferroelectric liquid crystal mixtures are preferably mixtures consisting of at least one optically active dopant and one liquid crystalline material. The latter consists of at least one achiral component, preferably a plurality of achiral components, which as a rule should have a broad tilted smectic phase, preferably an $S_C$ phase. The optically active dopants need not themselves be liquid crystalline but can preferably have a smectic or cholesteric phase. The optically active dopants should however induce in the liquid crystalline material a tilted smectic chiral phase having a suitable twist and a sufficiently high spontaneous polarization.

SUMMARY OF THE INVENTION

The present invention relates to compounds of the general formula

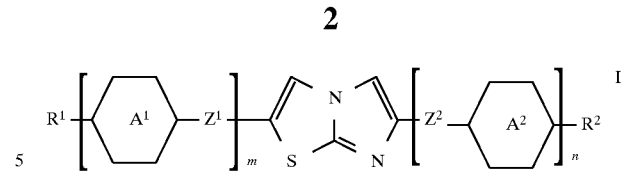

in which:

m and n are the number 0 or 1;

$R^1$ is a group $R^3$, a cyclic chiral group $Q^1$ or, if n is the number 0 and m is the number 1, also a group $R^3$-$A^3$-$Z^3$-, and $R^2$ is a group $R^4$, a cyclic chiral group $Q^2$ or, if m is the number 0 and n is the number 1, also a group $R^4$-$A^4$-$Z^4$;

the rings $A^1, A^2, A^3, A^4$ are trans-1,4-cyclohexylene or are 1,4-phenylene which is unsubstituted or monosubstituted or disubstituted by fluorine, chlorine, cyano or methyl;

$R^3$ and $R^4$ are each an alkyl or alkenyl radical in which one methylene group or two non-neighbouring methylene groups are optionally replaced by —O—, —COO— and/or —OOC—, and/or one or more hydrogen atoms are replaced by fluorine or chlorine;

$Z^1$, $Z^2$, $Z^3$ and $Z^4$, independenty of one another, are a single bond, $CH_2$—$CH_2$, O—$CH_2$, $CH_2$—O, COO, OOC, C≡C—, $(CH_2)_4$, $O(CH_2)_3$, CH=CH—$CH_2$O, $OCH_2$—CH=CH, CH=CH—$(CH_2)_2$ or $(CH_2)_2$—CH=CH;

and $Q^1$ and/or $Q^2$ are one of the following chiral groups:

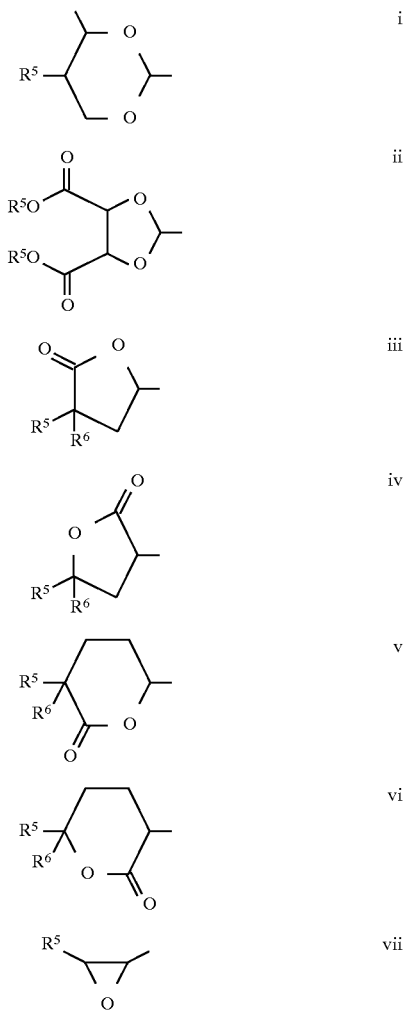

in which $R^5$ and $R^6$ are each an alkyl or alkenyl radical in which one methylene group or two non-neighbouring methylene groups are optionally replaced by —O—, —COO— and/or —OOC—, and/or one or more hydrogen atoms are replaced by fluorine or chlorine, with the proviso that any oxygen atoms present in $R^5$ and/or $R^6$ are not linked directly to the ring in $Q^1$ or $Q^2$.

It was found, surprisingly, that the compounds of the formula I, all of which have an imidazothiazole unit, have a pronounced tendency to form liquid crystalline phases, in particular to form tilted smectic phases. The optically inactive compounds of the formula I generally have a tilted smectic phase, especially an $S_C$ phase, in addition to a nematic and/or an $S_A$ phase. Many of the optically active compounds of the formula I have a tilted smectic chiral phase, especially an $S_C^*$ phase, in addition to a cholesteric and/or an $S_A$ phase. These compounds are therefore particularly suitable as components or chiral dopants of tilted smectic chiral phases in liquid crystal mixtures. However, they are also suitable as components or chiral dopants for nematic or cholesteric mixtures. The present invention thus offers a broad range of novel components and mixtures for further optimization and modification of liquid crystalline materials.

The compounds of the formula I have high chemical resistance and high stability to electric and magnetic fields. They are colourless, can be easily prepared and have sufficient solubility in one another and in known liquid crystalline materials.

DESCRIPTION OF THE INVENTION

The properties of the compounds of the formula I may vary within wide ranges, depending on the number and importance of the rings and of the substituents. For example, aromatic rings lead to higher, and saturated rings to lower, values of the optical anisotropy. An increase in the clear point can be achieved, for example, by introducing one or two further rings. Lateral halogen substituents make a contribution to the dielectric constant both parallel and perpendicular to the longitudinal molecular axis, which can be utilized for increasing or reducing the dielectric anisotropy, depending on the substitution pattern. Furthermore, by means of lateral substituents of one or more rings, the mesophase regions can be modified, any tendency to form highly ordered smectic phases can be substantially suppressed and often the solubility can also be improved.

The compounds according to the invention therefore permit further optimization of the liquid crystal mixtures and modification of the electro-optical properties of such mixtures in a wide range.

The expressions used in the definitions are explained as follows:

The expression "alkyl or alkenyl radical in which one methylene group or two non-neighbouring methylene groups are optionally replaced by —O—, —COO— and/or —OOC—, and/or one or more hydrogen atoms are replaced by fluorine or chlorine" includes straight-chain and branched (optionally chiral) radicals, such as alkyl, 1-alkenyl, 2-alkenyl, 3-alkenyl, 4-alkenyl, alkenyl having a terminal double bond, alkoxy, alkenyloxy, alkoxyalkyl, alkenyloxyalkyl, alkoxyalkenyl, alkylcarbonyloxy, alkylcarbonyloxyalkyl, alkoxycarbonylalkyl, alkoxyalkylcarbonyloxy, fluoroalkyl, difluoroalkyl, trifluoroalkyl, chloroalkyl, cyanoalkyl, methylalkyl, fluoroalkoxy, fluoroalkylcarbonyloxy, methylalkoxy, methylalkoxycarbonyl and the like.

Examples of preferred radicals are methyl, ethyl, propyl, butyl, pentyl, hexyl, heptyl, octyl, nonyl, decyl, undecyl, dodecyl, 1-methylpropyl, 1-methylheptyl, 2-methylheptyl, (Z)-2-pentenyl, (Z)-2-hexenyl, (Z)-2-heptenyl, (Z)-2-octenyl, (Z)-2-nonenyl, (E)-3-pentenyl, (E)-3-hexenyl, (E)-3-heptenyl, (E)-3-octenyl, (E)-3-nonenyl, (Z)-4-hexenyl, (Z)-4-heptenyl, (Z)-4-octenyl, (Z)-4-nonenyl; alkenyl groups having a terminal double bond, such as 3-butenyl, 4-pentenyl, 5-hexenyl, 6-heptenyl, 7-octenyl, 8-nonenyl; methoxy, ethoxy, propoxy, butoxy, pentyloxy, hexyloxy, heptyloxy, octyloxy, nonyloxy, 1-methylpropoxy, 1-methylheptyloxy, (E)-2-propenyloxy, (E)-2-butenyloxy, (E)-2-pentenyloxy, (E)-2-hexenyloxy, (E)-2- heptenyloxy, (E)-2-octenyloxy, (Z)-3-pentenyloxy, (Z)-3-hexenyloxy, (Z)-3-heptenyloxy, (Z)-3-octenyloxy, (Z)-3-nonenyloxy, (E)-4-hexenyloxy, (E)-4-heptenyloxy, (E)-4-octenyloxy, (E)-4-nonenyloxy; methoxyethyl, methoxypropyl, methoxybutyl, methoxypentyl, methoxyhexyl, methoxyheptyl, ethoxymethyl, propoxymethyl, butoxymethyl, pentyloxymethyl, hexyloxymethyl, ethoxyethyl, propoxyethyl, butoxyethyl, pentyloxyethyl, hexyloxyethyl, heptyloxyethyl, ethoxypropyl, propoxypropyl, butoxypropyl, pentyloxypropyl; 2-fluoropropyloxy, 2-fluoropentyloxy, 2-fluoroctyloxy, 2-chlorohexyloxy, 2-chloroctyloxy, butyl-carbonyloxy, pentylcarbonyloxy, hexylcarbonyloxy, heptylcarbonyloxy, 2-fluorobutylcarbonyloxy, 2-fluoropentylcarbonyloxy, 2-fluorohexylcarbonyloxy, 2-fluoroheptylcarbonyloxy 2-chlorobutylcarbonyloxy, 2-chloropentylcarbonyloxy, 2-chlorohexylcarbonyloxy, 2-chloroheptylcarbonyloxy, 2-methylpentylcarbonyloxy, 2-methylhexylcarbonyloxy, 2-methylheptylcarbonyloxy, 2-methylpentyloxycarbonyl, 2-methylhexyloxycarbonyl, 2-methylheptyloxycarbonyl, ethoxycarbonylmethoxy, propoxycarbonylmethoxy, butoxycarbonylmethoxy, pentyloxycarbonylmethoxy, hexyloxycarbonylmethoxy and the like.

Particularly preferred compounds of the formula I are those in which the radicals $R^3$ to $R^6$ have 3 to 12 carbon atoms. They may be straight-chain or branched. The radicals $R^3$ and $R^4$ are preferably straight-chain. However, those radicals $R^3$ and $R^4$ which lead to chiral side chains owing to branching and/or owing to the presence of a fluorine or chlorine substituent and lead to optical activity in the compounds of the formula I are also preferred. Particularly preferred chiral radicals $R^3$ and $R^4$ are 1-methylalkyl, 1-methylalkoxy, 1-methylalkoxycarbonyl, 2-fluoroalkoxy, 2-chloroalkoxy, 2-fluoroalkanoyloxy and 2-chloroalkanoyloxy. The radicals $R^5$ and $R^6$ are preferably straight-chain.

$Z^1$ is preferably a single bond, —CH$_2$CH$_2$—, —OCH$_2$— or —OOC—, $Z^2$ is preferably a single bond, —CH$_2$CH$_2$—, —CH$_2$O— or —COO—; $Z^3$ and $Z^4$ are preferably a single bond, —CH$_2$CH$_2$—, —CH$_2$O—, —OCH$_2$—, —COO— or —OOC—.

The rings $A^1$ to $A^4$ are preferably 1,4-phenylene, 1,4-phenylene monosubstituted or disubstituted by fluorine, and/or cyclohexylene. Preferred fluorine-substituted rings are 2-fluoro-1,4-phenylene, 3-fluoro-1,4-phenylene and 2,3-difluoro-1,4-phenylene. In general, those compounds of the formula I in which at least one of the rings $A^1$ or $A^2$ is 1,4-phenylene, 2-fluoro-1,4-phenylene, 3-fluoro-1,4-phenylene or 1,3-difluoro-1,4-phenylene are particularly preferred.

The chiral rings $Q^1$ and $Q^2$ occur in the compounds of the formula I preferably in one of two enantiomeric forms. Among the compounds of the formula I in which $Q^1$ and/or $Q^2$ occur, preferred compounds are consequently those in which $Q^1$ and/or $Q^2$ lead to optically active compounds of the formula I. The rings $Q^1$ and $Q^2$ can be identical or different but are preferably identical. Preferred compounds of the formula I in which $Q^1$ and/or $Q^2$ occur are those in which $Q^1$ and/or $Q^2$ are of the formulae i and/or ii.

Particularly preferred subgroups of the formula I are the compounds of the general formulae

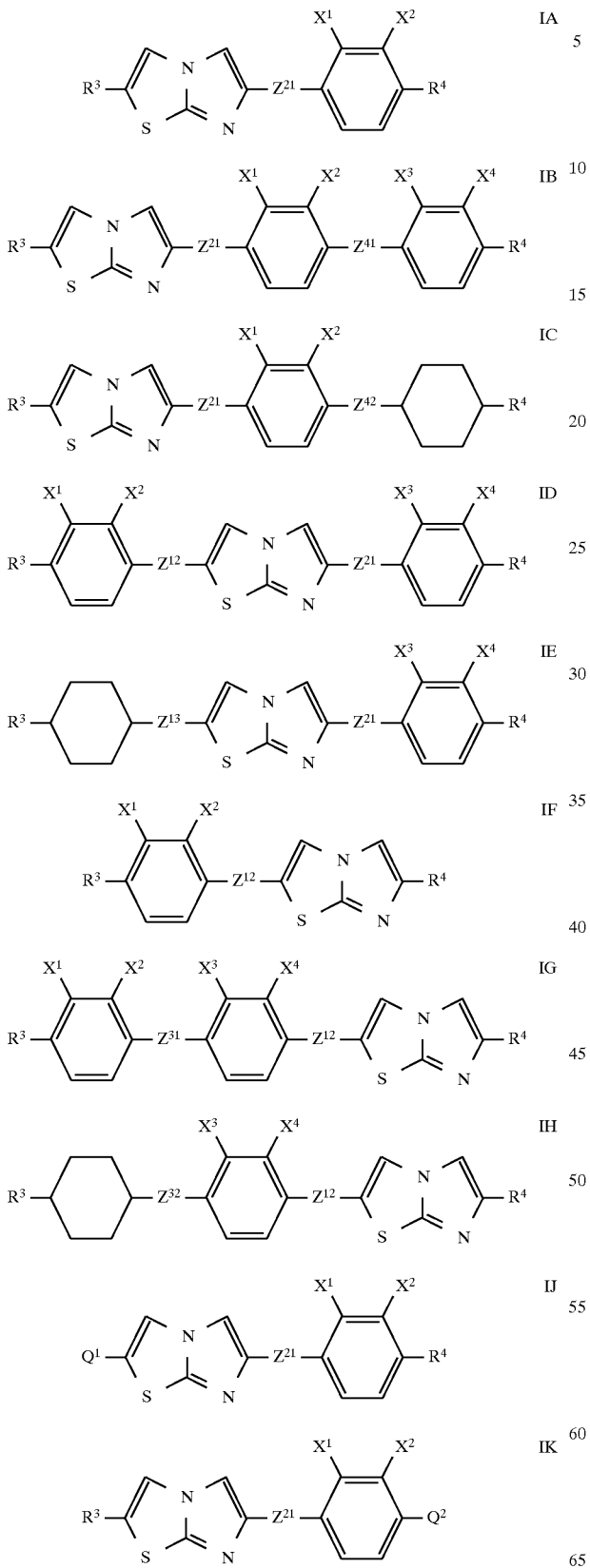

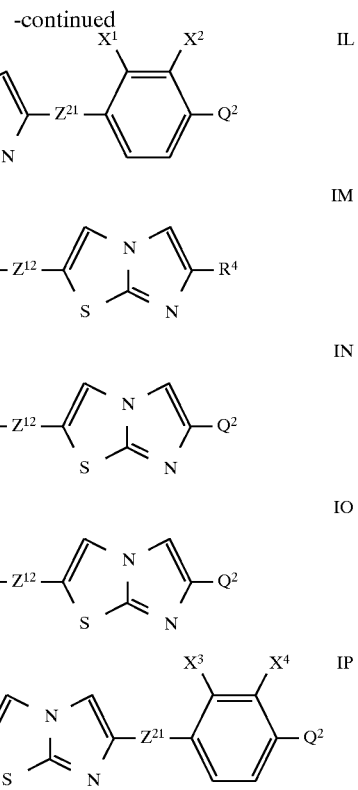

in which $Q^1$ and $Q^2$ as well as $R^3$ and $R^4$ have the abovementioned meaning, $Z^{12}$, $Z^{13}$, $Z^{21}$, $Z^{31}$, $Z^{32}$, $Z^{41}$ and $Z^{42}$ are a single bond and/or $CH_2CH_2$, $Z^{21}$ is furthermore $CH_2O$, $Z^{12}$ and $Z^{31}$ are furthermore $OCH_2$, $Z^{41}$ is furthermore $CH_2O$ or $OCH_2$, $Z^{32}$ is furthermore $CH_2O$ or $COO$ and $Z^{42}$ is furthermore $OCH_2$ or $OOC$, and the substituents $X^1$ to $X^4$ are hydrogen or fluorine. Preferably, in each case not more than one or two of the substituents $X^1$ to $X^4$ are not hydrogen and preferably not more than one of the groups $Z^{12}$ to $Z^{42}$ is not a single bond.

Among the compounds of the formulae IA to IP, very particularly preferred compounds are those which, in addition to the imidazothiazole unit and optionally present chiral rings $Q^1$ and/or $Q^2$ have only one further ring. These are the compounds of the formulae IA, IF and IJ to IO.

The imidazothiazoles of the general formula I can in general be prepared according to the following schemes.

An aldehyde of the general formula II is first reacted with sulphuryl chloride and thiourea to give an aminothiazole of the general formula III. This reaction has been described in the literature for analogous examples, for example in Helv. Chim. Acta 38, 1291 (1955). The aminothiazole of the formula III is then reacted, analogously to J. Chem. Soc. P. I, 1989, 643, with a bromoaceto derivative of the general formula V to give the immonium salt of the formula VI, which is cyclized to I without further purification by heating in a suitable solvent, such as, for example, ethanol. The bromoaceto compounds of the formula V are readily obtainable by α-bromination of the corresponding unbrominated aceto derivatives of the general formula IV, for example by means of copper(II) bromide. The reaction has been described in J. Org. Chem. 29, 3459 (1964), for analogous examples.

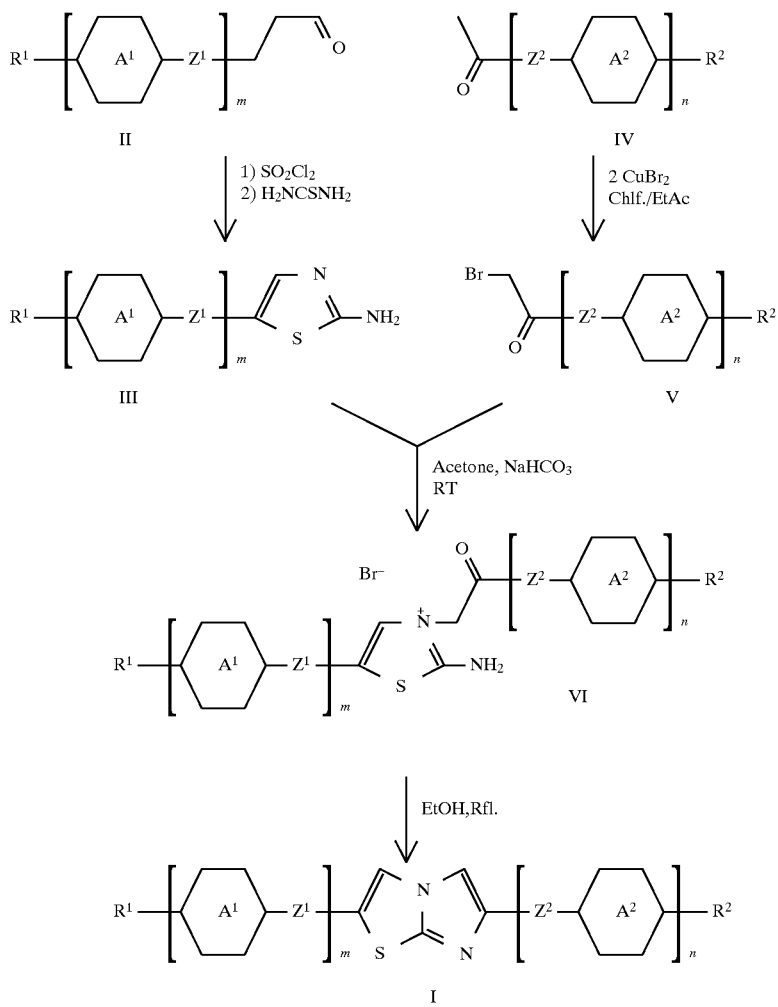

If ester groups are present in the group $R^1A^1Z^1$ and/or $R^2A^2Z^2$, the esterification is preferably not carried out until after the described formation of the imidazothiazole unit. Furthermore, if $R^1A^1Z^1$ and/or $R^2A^2Z^2$ have ether groups, if desired the etherification can also be carried out after the formation of the imidazothiazole unit.

The starting materials required for the synthesis of the compounds of the formula I are known compounds or analogues of known compounds or can be prepared from known compounds in a few steps. Many of the starting materials are also commercially available. Thus, for example, aldehydes can be prepared from suitable nitriles by reduction with DIBAH and, if required, can be extended by homologization reactions to give aldehydes of the formula II. Such nitriles, aldehydes and homologization reactions have been described, for example, in EP-A-0122389. The preparation of methylcarbonyls of the formula IV is also generally known to a person skilled in the art. Thus, for example, suitable methyl ketones are readily obtainable from corresponding nitrites by reaction with methyllithium or with a methylmagnesium halide, or also from aromatics by Friedel-Crafts acylation. Suitable nitrites have been described in large numbers in the literature on liquid crystals.

The compounds of the formula I can be used in the form of mixtures with one another and/or with other liquid crystalline components. The invention thus also relates to liquid crystalline mixtures having at least 2 components, wherein at least one component is a compound of the formula I. A second component and optionally further components may be further compounds of the general formula I or other suitable liquid crystalline components. The compounds of the formula I are preferably used as a component of mixtures which have a cholesteric and/or a tilted smectic phase, for example a chiral $S_C$ phase. The compounds of the formula I may be used as achiral components and/or as chiral dopants.

Suitable liquid crytalline components which may be used, in addition to the compounds of the formula I, in the mixtures according to the invention are known in large numbers to a person skilled in the art, for example from D. Demus et al., Flussige Kristalle in Tabellen [Liquid crystals in tables], VEB Deutscher Verlag für Grundstoffindustrie, Leipzig, Volumes I and II, or from Landolt-Börnstein, Liquid Crystals, Volumes IV 7a–d, and many of them are also commercially available.

Owing to the good solubility of the compounds, according to the invention, of the formula I in other liquid crystalline materials and owing to their good miscibility with one another, the proportion of compounds of the formula I in the mixtures according to the invention can be relatively high and may be, for example, 0.1–50% by weight. If achiral compounds of the formula I are used as components, in general a proportion of about 1–40% by weight, in particular of 3–30% by weight, is preferred. The proportion of chiral dopants is substantially determined by the twisting capacity, the spontaneous polarization and the desired pitch of the mixture. The proportion of one or more optionally used chiral dopants of the formula I may therefore vary within a wide range depending on the appliation and may be, for example, about 0.1–40% by weight. For display apparatuses based on liquid crystals having tilted smectic phases, a proportion of about 1–30% by weight, in particular of about 3–25% by weight, of optically active dopants of the formula I is generally preferred.

The mixtures according to the invention preferably contain, in addition to one or more compounds of the formula I, at least one further compound from the group consisting of compounds of the general formulae $R^7$ and $R^8$, independently of one another, are alkyl, alkenyl, alkoxy, alkenyloxy, alkoxyalkyl, alkoxyalkoxy, alkanoyloxy, alkenoyloxy, alkoxycarbonyl, alkenyloxycarbonyl;

$R^9$ and $R^{12}$, independently of one another, are alkyl or alkenyl;

$R^{10}$ und $R^{11}$, independently of one another, are alkyl, alkenyl, alkoxy and/or alkenyloxy;

$Z^5$, $Z^6$ and $Z^7$, independently of one another, are a single bond, $CH_2$—$CH_2$ or $CH_2O$, and $Z^6$ is furthermore $OCH_2$, COO or OOC;

E and F, independently of one another, are phenylene-1,4-diyl or trans-cyclohexylene-1,4-diyl;

$X^1$ and $X^2$, independently of one another, are hydrogen or fluorine;

(R*) and (S*) denote the relative configurations.

The compounds of the formulae XIII to XVII are optically active dopants which, depending on the desired effect, may

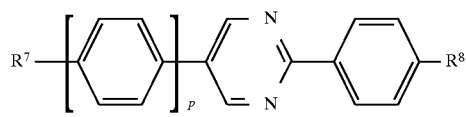 VII

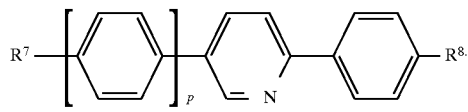 VIII

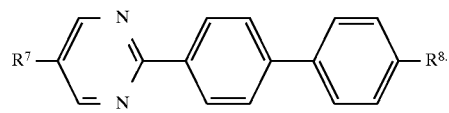 IX

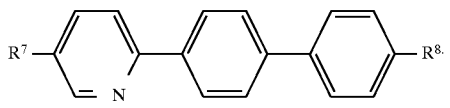 X

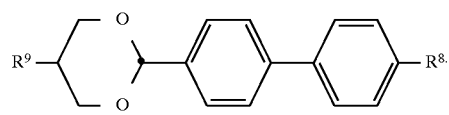 XI

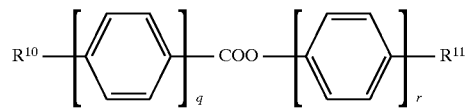 XII

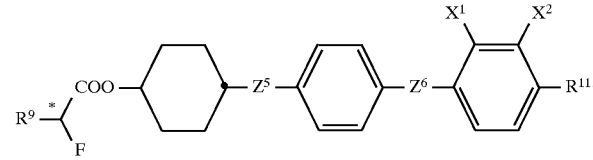 XIII

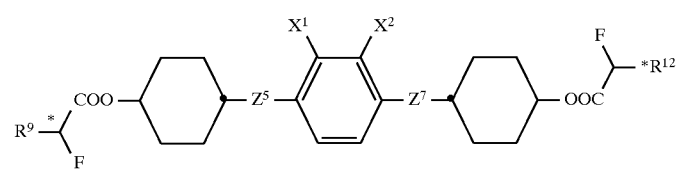 XIV

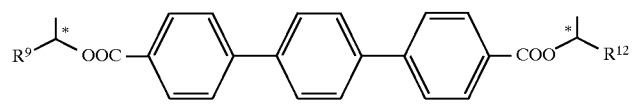 XV

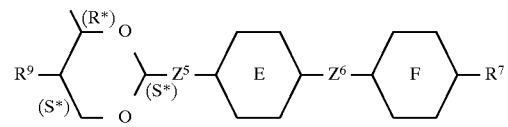 XVI

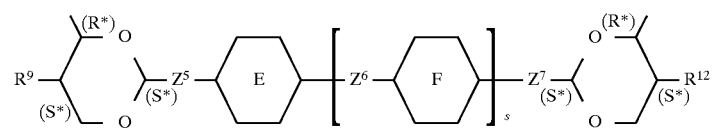 XVII in which p is 0 or 1;

q and r are 1 or 2, q+r=2 or 3;

s is 0, 1 or 2;

be present in one of the two enantiomeric forms in the mixture, in addition to one or more compounds of the formula I.

The substituents $R^7$ to $R^{12}$ preferably each have not more than 18 carbon atoms; about 5–12 carbon atoms are particularly preferred; the substituents $R^7$ to $R^{12}$ may be linear or branched but are preferably linear.

The preparation of liquid crystalline mixtures and electro-optical apparatuses can be carried out in a manner known per se.

The preparation of compounds of the formula I and liquid crystalline mixtures of the type according to the invention are further illustrated by the following Examples. Optical antipodes of the compounds of the formula I each have the same phase transformation temperatures and induce the same absolute values of the spontaneous polarization and of the twisting, but with opposite signs. The abbreviations used for characterizing the phase transformations have the following meanings:

| C | crystalline |
|---|---|
| S | smectic, |
| $S_A$, $S_B$, $S_C$, etc. | smectic A, B, C, etc., |
| $S_C^*$, $S_F^*$, etc. | chiral smectic C, F, etc. |
| N | nematic, |
| N* | cholesteric, |
| I | isotropic. |

EXAMPLE 1 a) 50 ml of ethyl acetate were added to 32.1 g of finely ground copper(II) bromide and refluxing was carried out for 30 minutes. A hot solution of 8.3 g of p-hydroxyacetophenone in 50 ml of chloroform was added dropwise to the boiling reaction mixture and refluxing was continued for 5 hours. The cooled mixture was then filtered, the residue was thoroughly washed with ethyl acetate and the filtrate was refluxed briefly with active carbon and then cooled and filtered. The principal amount of the solvent was evaporated off under reduced pressure and the crystals formed were filtered off with suction and dried under greatly reduced pressure. This gave 8.1 g of 2-bromo-1-(4-hydroxyphenyl)ethanone as pale brown crystals of melting point 122°–124° C.

b) 20 g of sulphuryl chloride were added dropwise to 21.3 g of nonanal in such a way that the reaction temperature remained between 25°–28° C. The reaction solution was then stirred at room temperature for 16 hours, after which 11.4 g of thiourea were added and refluxing was carried out for 3 hours at about 90° C. 200 ml of water were then added dropwise to the still boiling reaction solution, and the reaction mixture was kept at 90° C. for a further hour. The reaction mixture was then filtered hot, cooled and extracted with ether, and the aqueous phase separated off was adjusted to pH 10 with 2N sodium hydroxide. This phase was then extracted with ether, the ether phase was dried over sodium sulphate, the ether was evaporated off and the solid residue was recrystallized from cyclohexane. This gave 8 g of 2-amino-5-heptylthiazole as colourless lamellae of melting point 75°–76° C.

c) A solution of 7.3 g of 2-bromo-1-(4-hydroxyphenyl) ethanone in 30 ml of dry acetone was added dropwise to a solution of 7.4 g of 2-amino-5-heptylthiazole in 30 ml of dry acetone at room temperature. Thereafter, the reaction mixture was stirred at room temperature for 16 hours and the solvent was then removed under reduced pressure. A two-phase mixture of 300 ml of methylene chloride and 300 ml of 1M sodium bicarbonate solution was added to the residue and the mixture was stirred vigorously for 20 minutes at room temperature. The precipitated solid was then filtered off with suction, dried under reduced pressure and, directly thereafter, refluxed in 100 ml of ethanol for 24 hours.

Thereafter, cooling was carried out, the solvent was evaporated off under reduced pressure, the residue was taken up in ethyl acetate and the mixture was filtered with silica gel. The filtrate was then evaporated and the solid residue was recrystallized from ethyl acetate/cyclohexane. This gave 2.6 g of 2-heptyl-6-(4-hydroxyphenyl)imidazo[2,1-b]thiazole as yellowish crystals of melting point 122° C.

The following compounds can be prepared in an analogous manner:

2-pentyl-6-(4-nonylphenyl)imidazo[2,1-b]thiazole, m.p.(C/$S_A$): 89.7° C., C.p.($S_A$/I): 127.4° C.;
2-hexyl-6-(4-octylphenyl)imidazo[2,1-b]thiazole;
2-hexyl-6-(4-nonylphenyl)imidazo[2,1-b]thiazole, m.p.(C/$S_C$): 84.1° C., $S_F/S_C$: 80.8° C., $S_C/S_A$: 96.2° C., c.p.($S_A$/I): 124.7° C.;
2-hexyl-6-(4-decylphenyl)imidazo[2,1-b]thiazole;
2-heptyl-6-(4-heptylphenyl)imidazo[2,1-b]thiazole;
2-heptyl-6-(4-octylphenyl)imidazo[2,1-b]thiazole;
2-heptyl-6-(4-nonylphenyl)imidazo[2,1-b]thiazole, m.p.(C/$S_C$): 86.8° C., $S_C/S_A$: 112.7° C., c.p.($S_A$/I): 129° C.;
2-heptyl-6-(4-decylphenyl)imidazo[2,1-b]thiazole;
2-octyl-6-(4-heptylphenyl)imidazo[2,1-b]thiazole;
2-octyl-6-(4-octylphenyl)imidazo[2,1-b]thiazole;
2-octyl-6-(4-nonylphenyl)imidazo[2,1-b]thiazole;
2-octyl-6-(4-decylphenyl)imidazo[2,1-b]thiazole;
2-nonyl-6-(4-heptylphenyl)imidazo[2,1-b]thiazole;
2-nonyl-6-(4-octylphenyl)imidazo[2,1-b]thiazole;
2-nonyl-6-(4-nonylphenyl)imidazo[2,1-b]thiazole;
2-nonyl-6-(4-decylphenyl)imidazo[2,1-b]thiazole;
2-decyl-6-(4-heptylphenyl)imidazo[2,1-b]thiazole;
2-decyl-6-(4-octylphenyl)imidazo[2,1-b]thiazole;
2-decyl-6-(4-nonylphenyl)imidazo[2,1-b]thiazole;
2-heptyl-6-(2-fluoro-4-nonylphenyl) imidazo[2,1-b] thiazole;
2-heptyl-6-(3-fluoro-4-nonylphenyl)imidazo[2,1-b]thiazole;
2-heptyl-6-(2,3-difluoro-4-nonylphenyl)imidazo[2,1-b]-thiazole;
2-heptyl-6-[2-(4-nonylphenyl)ethyl]imidazo[2,1-b]thiazole;
2-heptyl-6-(trans-4-heptylcyclohexyl)imidazo[2,1-b]-thiazole, m.p.(C/$S_A$): 71° C., $S_1/S_A$: 61.8° C., c.p.($S_A$/I): 71.7° C.;
2-heptyl-6-[2-(trans-4-nonylcyclohexyl)ethyl]imidazo [2,1-b]thiazole;
2-heptyl- 6-(4'-nonylbiphenylyl)imidazo[2,1-b]thiazole;
2-heptyl-6-(2',3'-difluoro-4'-nonylbiphenylyl)imidazo-[2,1-b]thiazole;
2-heptyl- 6-[4-(trans-4-nonylcyclohexyl)phenyl]imidazo-[2,1-b]thiazole;
2-heptyl-6-{4-[2-(trans-4-octylcyclohexyl)ethyl]phenyl}-imidazo[2,1-b]thiazole;
2-(4-heptylphenyl)-6-heptylimidazo[2,1-b]thiazole;
2-(4-heptylphenyl)-6-octylimidazo[2,1-b]thiazole;
2-(4-heptylphenyl)-6-nonylimidazo[2,1-b]thiazole;
2-(4-heptylphenyl)-6-decylimidazo[2,1-b]thiazole;
2-(4-octylphenyl)-6-heptylimidazo[2,1-b]thiazole;
2-(4-octylphenyl)-6-octylimidazo[2,1-b]thiazole;
2-(4-octylphenyl)-6-nonylimidazo[2,1-b]thiazole;
2-(4-octylphenyl)-6-decylimidazo[2,1-b]thiazole;
2-(4-nonylphenyl)-6-heptylimidazo[2,1-b]thiazole;
2-(4-nonylphenyl)-6-octylimidazo[2,1-b]thiazole;
2-(4-nonylphenyl)-6-nonylimidazo[2,1-b]thiazole;
2-(4-decylphenyl)-6-heptylimidazo[2,1-b]thiazole;
2-(4-decylphenyl)-6-octylimidazo[2,1-b]thiazole;
2-(2-fluoro-4-heptylphenyl) -6-nonylimidazo[2,1-b] thiazole;
2-(3-fluoro-4-heptylphenyl)-6-nonylimidazo[2,1-b]thiazole;
2-(2,3-difluoro-4-heptylphenyl)-6-nonylimidazo[2,1-b]-thiazole;

2-[2-(4-heptylphenyl)ethyl]-6-nonylimidazo[2,1-b]thiazole;
2-(trans-4-heptylcyclohexyl)-6-nonylimidazo[2,1-b]-thiazole;
2-[2-(trans-4-heptylcyclohexyl)ethyl]-6-heptylimidazo-[2,1-b]thiazole;
2-(4'-heptylbiphenylyl)-6-nonylimidazo[2,1-b]thiazole;
2-(2',3'-difluoro-4'-heptylbiphenyl)-6-nonylimidazo [2,1-b]thiazole;
2-[4-(4-trans-heptylcyclohexyl)phenyl]-2-nonylimidazo-[2,1-b]thiazole;
2-{4-[2-(trans-4-heptylcyclohexyl)ethyl]phenyl}-6-octyl-imidazo[2,1-b]thiazole;
2-(4-nonylphenyl)-6-(4-heptylphenyl)imidazo[2,1-b]-thiazole;
2-(2,3-difluoro-4-nonylphenyl)-6-(4-heptylphenyl)imidazo-[2,1-b]thiazole;
2-(4-nonylphenyl)-6-(2,3-difluoro-4-heptylphenyl)imidazo-[2,1-b]thiazole.

EXAMPLE 2

A mixture of 0.314 g of 2-heptyl-6-(4-hydroxyphenyl) imidazo[2,1-b]thiazole (preparation analogous to Example 1), 0.11 g of potassium hydroxide and 0.29 g of bromooctane in 15 ml of ethanol/water (2:1) was refluxed for 16 hours. Thereafter, the reaction mixture was cooled and extracted with ether and the organic phase was dried over sodium sulphate, filtered and evaporated. The residue was then recrystallized from absolute ethanol. This gave 0.348 g of 2-heptyl-6-(4-octyloxyphenyl)imidazo[2,1-b]thiazole as colourless crystals, m.p.(C/$S_1$): 61° C., $S_1/S_2$: 113° C., $S_2/S_3$ 115.3° C., $S_3/S_C$: 121.7° C., c.p.($S_C$/I): 148.9° C.

The following compounds can be prepared in an analogous manner:
2-heptyl-6-(4-heptyloxyphenyl)imidazo[2,1-b]thiazole;
(R)-2-heptyl-6-[4-(2-octyloxy)phenyl]imidazo[2,1-b] thiazole;
(S)-2-heptyl-6-[4-(2-octyloxy)phenyl]imidazo[2,1-b] thiazole;
2-heptyl-6-[4-((E)-2-octenyloxy)phenyl]imidazo[2,1-b]-thiazole;
2-heptyl-6-[4-((Z)-3-octenyloxy)phenyl]imidazo[2,1-b]-thiazole;
2-heptyl-6-[4-((E)-4-octenyloxy)phenyl]imidazo[2,1-b] thiazole;
2-heptyl-6-[4-(7-octenyloxy)phenyl]imidazo[2,1-b] thiazole;
2-heptyl-6-(4-nonyloxyphenyl)imidazo[2,1-b]thiazole;
2-hexyl-6-(4-octyloxyphenyl)imidazo[2,1-b]thiazole;
(R)-2-hexyl-6-[4-(2-octyloxy)phenyl]imidazo[2,1-b] thiazole;
2-hexyl-6-(4-nonyloxyphenyl)imidazo[2,1-b]thiazole;
2-octyl-6-(4-heptyloxyphenyl)imidazo[2,1-b]thiazole;
2-octyl-6-(4-octyloxyphenyl)imidazo[2,1-b]thiazole; m.p. (C/$S_1$): 65° C., $S_1/S_2$: 85° C., $S_2/S_3$ 107° C., $S_3/S_C$: 120.5° C., c.p.($S_C$/I): 149° C.;
(S)-2-octyl-6-[4-(2-octyloxy)phenyl]imidazo[2,1-b] thiazole;
2-octyl-6-(4-nonyloxyphenyl)imidazo[2,1-b]thiazole;
2-nonyl-6-(4-heptyloxyphenyl)imidazo[2,1-b]thiazole;
2-nonyl-6-(4-octyloxyphenyl)imidazo[2,1-b]thiazole; m.p. (C/$S_1$): 68° C., $S_1/S_2$: 99.5° C., $S_2/S_3$ $_{120°}$ C., $S_3/S_C$: 124.5° C., c.p.($S_C$/I): 151.5° C.;
(S)-2-nonyl-6-[4-(2-octyloxy)phenyl]imidazo[2,1-b] thiazole;
2-heptyl-6-(2-fluoro-4-octyloxyphenyl)imidazo[2,1-b] thiazole;
(S)-2-octyl-6-[2-fluoro-4-(2-octyloxy)phenyl]imidazo[2,1-b]thiazole;
2-heptyl-6-(3-fluoro-4-octyloxyphenyl)imidazo[2,1-b] thiazole;
(S)-2-octyl-6-[3-fluoro-4-(2-octyloxy)phenyl]imidazo[2,1-b]thiazole;
2-heptyl-6-(2,3-difluoro-4-octyloxyphenyl)imidazo[2,1-b]-thiazole;
(S)-2-octyl-6-[2,3-difluoro-4-(2-octyloxy)phenyl]imidazo-[2,1-b]thiazole;
2-heptyl-6-[2-(4-octyloxyphenyl)ethyl]imidazo[2,1-b] thiazole;
2-nonyl-6-[(4-heptylphenoxy)methyl]imidazo[2,1-b] thiazole;
2-octyl-6-(4l-octyloxybiphenyl)imidazo[2,1-b]thiazole;
2-octyl-6-(2', 3'-difluoro-4'-octyloxybiphenyl)imidazo[2,1-b]thiazole;
(S)-2-octyl-6-[2',3'-difluoro-4'-(2-octyloxy)biphenyl]-imidazo[2,1-b]thiazole;
2-heptyl-6-{4-[(trans-4-octylcyclohexyl)methoxy] phenyl}imidazo[2,1-b]thiazole;
2-(4-heptyloxyphenyl)-6-heptylimidazo[2,1-b]thiazole;
2-(4-heptyloxyphenyl)-6-octylimidazo[2,1-b]thiazole;
2-(4-heptyloxyphenyl)-6-nonylimidazo[2,1-b]thiazole;
2-(4-heptyloxyphenyl)-6-decylimidazo[2,1-b]thiazole;
2-(4-octyloxyphenyl)-6-heptylimidazo[2,1-b]thiazole;
2-(4-octyloxyphenyl)-6-octylimidazo[2,1-b]thiazole;
(S)-2-[4-4-(2-octyloxy)phenyl]-6-octylimidazo[2,1-b] thiazole;
2-[4-((E)-2-octenyloxy)phenyl]-6-heptylimidazo[2,1-b] thiazole;
2-[4-((Z)-3-octenyloxy)phenyl]-6-heptylimidazo [2,1-b-]-thiazole;
2-[4-((E)-4-octenyloxy)phenyl]-6-heptylimidazo[2,1-b]-thiazole;
2-(4-nonyloxyphenyl)-6-heptylimidazo [2,1-b]thiazole;
2-(4-nonyloxyphenyl)-6-octylimidazo [2,1-b]thiazole;
2-(2-fluoro-4-octyloxyphenyl)-6-octylimidazo[2,1-b] thiazole;
2-(3-fluoro-4-oatyloxyphenyl)-6-octylimidazo [2,1-b] thiazole;
(S)-2-[3-fluoro-4-(2-octyloxy)phenyl]-6-octylimidazo[2,1-b]thiazole;
2-(2,3-difluoro-4-octyloxyphenylphenyl)-6-octylimidazo[2,1-b]thiazole;
2-[2-(4-heptylphenyl)ethyl]-6-nonylimidazo[2,1-b]thiazole;
2-(trans-4-heptylcyclohexyl)-6-nonylimidazo[2,1-b] thiazole;
2-[2-(trans-4-heptylcyclohexyl)ethyl]-6-heptylimidazo[2,1-b]thiazole;
2-(4'-heptylbiphenylyl)-6-nonylimidazo[2,1-b]thiazole;
2-(2',3'-difluoro-4'-heptylbiphenylyl)-6-nonylimidazo [2,1-b]thiazole;
2-{4-[(trans-4-octylcyclohexyl)methoxy]phenyl}-2-heptylimidazo[2,1-b]thiazole;
2-(4-octylphenyl)-6-(4-octyloxyphenyl)imidazo[2,1-b] thiazole;
2-(4-octyloxyphenyl)-6-(4-octylphenyl)imidazo[2,1-b] thiazole;
2-(2,3-difluoro-4-octyloxyphenyl)-6-(4-octylphenyl) imidazo-[2,1-b]thiazole;
2-(4-octyloxyphenyl)-6-(2,3-difluoro-4-octylphenyl) imidazo-[2,1-b]thiazole;
2-(4-octyloxyphenyl)-6-(2,3-difluoro-4-octyloxyphenyl) imidazo[2,1-b]thiazole;
2-(2,3-difluoro-4-octyloxyphenyl)-6-(4-octyloxyphenyl) imidazo[2,1-b]thiazole;
(S,S)-2-[4-(2-octyloxy)phenyl]-6-[4-(2-octyloxy)phenyl] imidazo[2,1-b]thiazole.

EXAMPLE 3 a) A mixture of 2 g of ethyl 2-heptylimidazo[2,1-b]thiazole-6-carboxylate, prepared from ethyl α-bromopyruvate analogously to Example 1, in 50 ml of 1N methanolic KOH is allowed to stand overnight at room temperature, then acidified with 1N sulphuric acid, diluted with 200 ml of water and then extracted with ether. The ether phase is then dried over sodium sulphate, filtered and evaporated. This gives 2-heptylimidazo[2,1-b]thiazole-6-carboxylic acid.

b) 1.2 g of N,N'-dicyclohexylcarbodiimide are added in portions to a solution of 1.3 g of 2-heptylimidazo[2,1-b]-thiazole-6-carboxylic acid, 1 g of 4-octyloxyphenol and 0.1 g of 4-(dimethylamino)pyridine in 25 ml of dichloromethane within 10 minutes while stirring. The mixture is stirred overnight at room temperature and then filtered. The filtrate is diluted with dichloromethane, washed with two portions of 50 ml each of saturated sodium carbonate solution and then with water, dried over magnesium sulphate and filtered, and the filtrate is evaporated. Recrystallization of the residue from ethyl acetate/cyclohexane gives 4-octyloxyphenyl 2-heptylimidazo[2,1-b]thiazole-6-carboxylate, m.p.(C/$S_A$): 112.6° C., c.p.($S_A$/I): 151.4° C.

The following can be prepared in an analogous manner:
4-(2-octyloxy)phenyl(S)-2-heptylimidazo[2,1-b]thiazole-6-carboxylate;
4-octylphenyl 2-heptylimidazo[2,1-b]thiazole-6-carboxylate;
octyl 2-(4-octylphenyl)imidazo[2,1-b]thiazole-6-carboxylate;
octyl 2-(4-octyloxyphenyl)imidazo[2,1-b]thiazole-6-carboxylate;
2-octyl (S)-2-(4-octyloxyphenyl)imidazo[2,1-b]thiazole-6-carboxylate;
(S)-2-octyl 2-[4-((S)-2-octyloxy)phenyl]imidazo[2,1-b]thiazole-6-carboxylate;
(R)-2-octyl 2-[4-((S)-2-octyloxy)phenyl]imidazo[2,1-b]thiazole-6-carboxylate;
octyl 4-(2-heptylimidazo[2,1-b]thiazol-6-yl)benzoate, m.p. (C/$S_1$): 61.8° C., $S_1$/$S_A$: 97° C., c.p.($S_A$/I): 129° C.;
2-octyl (S)-4-(2-octylimidazo[2,1-b]thiazol-6-yl)benzoate;
octyl 4-(6-heptylimidazo[2,1-b]thiazol-2-yl)benzoate;
octyl (R)-4-(6-heptylimidazo[2,1-b]thiazol-2-yl)benzoate, m.p.(C/I): 112.4° C.;
2-octyl (S)-4-(6-octylimidazo[2,1-b]thiazol-2-yl)benzoate;
2-octyl (S,S)-2-[4-(2-octyloxycarbonyl)phenyl]imidazo[2,1-b]thiazole-6-carboxylate;
2-octyl (S,S)-6-[4-(2-octyloxycarbonyl)phenyl]imidazo[2,1-b]thiazole-2-carboxylate, m.p.(C/N*): 62.7° C., c.p. (N*/I): 66.2° C.;
4-(2-heptylimidazo[2,1-b]thiazol-6-yl)phenyl nonanecarboxylate, m.p.(C/$S_C$): 92.7° C., $S_C$/$S_A$: 119° C., c.p.($S_A$/I): 147° C.;
4-(2-octylimidazo[2,1-b]thiazol-6-yl)phenyl octanecarboxylate;
4-(2-nonylimidazo[2,1-b]thiazol-6-yl)phenyl octanecarboxylate;
4-(2-octylimidazo[2,1-b]thiazol-6-yl)phenyl nonanecarboxylate;
2,3-difluoro-4-(2-heptylimidazo[2,1-b]thiazol-6-yl)phenyl decanecarboxylate, m.p.(C/N): 85.1° C., N/$S_C$: 90.2° C., c.p.($S_C$/I): 96.6° C.;
4-(2-octylimidazo[2,1-b]thiazol-6-yl)phenyl trans-4-heptylcyclohexanecarboxylate;
4-[2-(4-octylphenyl)imidazo[2,1-b]thiazol-6-yl]phenyl nonanecarboxylate;
4-(2-octylimidazo[2,1-b]thiazol-6-yl)phenyl (R)-2-fluorohexanecarboxylate;
2,3-difluoro-4-(2-octylimidazo[2,1-b]thiazol-6-yl)phenyl (R)-2-fluorohexanecarboxylate, m.p.(C/$S_A$): 88.3° C., c.p. ($S_A$/I): 91.8° C.;
4-(2-octylimidazo[2,1-b]thiazol-6-yl)phenyl (R)-2-chlorohexanecarboxylate;
4-(6-nonylimidazo[2,1-b]thiazol-2-yl)phenyl heptanecarboxylate;
4-(6-octylimidazo[2,1-b]thiazol-2-yl)phenyl octanecarboxylate;
4-(6-heptylimidazo[2,1-b]thiazol-2-yl)phenyl nonanecarboxylate;
4-(6-nonylimidazo[2,1-b]thiazol-2-yl)phenyl (R)-2-fluorohexanecarboxylate;
4-(6-octylimidazo[2,1-b]thiazol-2-yl)phenyl (R)-2-chlorohexanecarboxylate;
4-(6-octylimidazo[2,1-b]thiazol-2-yl)phenyl trans-4-heptylcyclohexanecarboxylate;
4-[6-(4-octylphenyl)imidazo[2,1-b]thiazol-2-yl]phenyl nonanecarboxylate.

EXAMPLE 4

A mixture of 0.08 g of 4-(2-carboxyimidazo[2,1-b]thiazol-6-yl)benzaldehyde, 0.133 g of (2R,3S)-2-octyl-1,3-butandiole (preparation: cf. EP-A-0 457 105), 15 ml of toluene and 3 drops of 2N sulphuric acid was refluxed for 2 hours with separation of water. Thereafter, cooling was carried out, 1 ml of triethylamine was added and partition was effected between ether and saturated sodium bicarbonate solution. The organic solution was then dried over magnesium sulphate, filtered and evaporated to dryness, and the residue was chromatographed over silica gel using toluene/ethyl acetate (10:1). Subsequent crystallization from ethyl acetate/hexane (1:3) gave 0.079 g of 2-((2R,3S,5R)-4-methyl-5-octyl-1,3-dioxan-2-yl)-6-[4-((2R,3S,5R)-4-methyl-5-octyl-1,3-dioxan-2-yl)phenyl]imidazo[2,1-b]thiazole, m.p.(C/$S_A$): 179° C., c.p.($S_A$/I): 191.2° C.

The following can be prepared in an analogous manner:
2-((2S, 3R, 5S)-4-methyl-5-octyl-1,3-dioxan-2-yl)-6-[4-((2S, 3R, 5S)-4-methyl-5-octyl-1,3-dioxan-2-yl)-phenyl]imidazo[2,1-b]thiazole;
2-((2R,3S,5R)-4-methyl-5-hexyl-1,3-dioxan-2-yl)-6-[4-((2R,3S,5R)-4-methyl-5-hexyl-1,3-dioxan-2-yl)-phenyl]imidazo[2,1-b]thiazole;
2-((2R,3S,5R)-4-methyl-5-decyl-1,3-dioxan-2-yl)-6-[4-((2R,3S,5R)-4-methyl-5-decyl-1,3-dioxan-2-yl)-phenyl]imidazo[2,1-b]thiazole;
2-((4R,5R)-4,5-dimethoxycarbonyl-1,3-dioxolanyl)-6-[4-((4R,5R)-4,5-dimethoxycarbonyl-1,3-dioxolanyl)]-imidazo[2,1-b]thiazole;
2-((4S,S)-4,5-dimethoxycarbonyl-1,3-dioxolanyl)-6-[4-((4S,5S)-4,5-dimethoxycarbonyl-1,3-dioxolanyl)]-imidazo[2,1-b]thiazole;
2-((4R,5SR)-4,5-diethoxycarbonyl-1,3-dioxolanyl)-6-[4-((4R,SR)-4,5-diethoxycarbonyl-,3-dioxolanyl)]-imidazo[2,1-b]thiazole;

EXAMPLE 5

To investigate the properties of the compounds of the formula I in mixtures, test mixtures were prepared. For this purpose, the component of the formula I which was to be tested was mixed with base mixture (BM). For comparison purposes, a comparative mixture was also prepared, one of its components being admixed, as a comparative component, with the base mixture BM. The phase sequence of these mixtures and the spontaneous polarization ($P_s$ in $nC/cm^2$) were determined, and the switching time and the switching angle were measured. The measurements were carried out under the following conditions: $P_s$ at $8.5\mu$ cell thickness and a delta voltage of 10 Hz and 5 V/$\mu$; switching times at 10 V/$\mu$ square-wave voltage (peak/peak) determined as time to $I_{max}$ and switching angle at $2\mu$ cell thickness and a voltage of 25 V. A temperature of 25° C. was maintained for all measurements.

Base mixture (BM)
16.6% by wt. of trans-4-[4-(2,3-difluoro-4-octyloxy-benzoyloxy)phenyl]cyclohexyl (R)-2-fluorohexanoate;
23.8% by wt. of 2-(4-hexyloxyphenyl)-5-nonylpyrimidine;
23.4% by wt. of 2-(4-nonyloxyphenyl)-5-nonylpyrimidine;
11.8% by wt. of 2-(4-nonyloxyphenyl)-5-octylpyrimidine;
12.1% by wt. of 2-(4-heptyloxyphenyl)-5-heptyl-pyrimidine;
12.3% by wt. of 2-(4-decyloxyphenyl)-5-octylpyrimidine;
Phase sequence [°C]:
I - 74.6 - N* - 67.7 - $S_A$ - 60.6-$S_C$* - −7.6 C Comparative mixture
15.0% by wt. of 2-(4-nonyloxyphenyl)-5-nonylpyrimidine;
85.0% by wt. of BM;
Phase sequence [°C]:
I - 71.0 - N* - 66.0 - $S_A$ - 60.0 - $S_C$* - ;
$P_s$: 16.0 $nC/cm^2$, switching time: 120 $\mu$s, switching angle: 50.2°.

Test mixture 1
15.0% by wt. of 2-heptyl-6-(4-nonylphenyl)imidazo-[2,1-b]-thiazole;
85.0% by wt. of BM;
Phase sequence [°C]:
I - 76.7 - N* - 74.5 - $S_A$ - 61.7 - $S_C$* - ;
$P_s$: 17.7 $nC/cm^2$, switching time: 100 $\mu$s, switching angle: 40°

Test mixture 2
15.0% by wt. of 2-hexyl-6-(4-nonylphenyl)imidazo[2,1-b]-thiazole;
85.0% by wt. of BM;
Phase sequence:
I - 74.4 - N* - 71.4 - $S_A$ - 60.3 - $S_C$* - ;
$P_s$: 16.8 $nC/cm^2$, switching time: 132 $\mu$s, switching angle: 52.1°.

Testmixture 3
15.0% by wt. of 2-pentyl-6-(4-nonylphenyl)imidazo-[2,1-b]thiazole;
85.0% by wt. of BM;
Phase sequence [°C]:
I - 76.1 - N* - 73.0 - $S_A$ - 59.9 - $S_C$* - ;
$P_s$: 16.1 $nC/cm^2$, switching time: 132 $\mu$s, switching angle: 51.3°.

Test mixture 4
15.0% by wt. of 2-heptyl-6-(4-octyloxyphenyl)imidazo-[2,1-b]thiazole; 85.0% by wt. of BM;
Phase sequence [°C]:
I - 80.9 - N* - 75.3 - $S_A$ - 70.6 - $S_C$* - ;
$P_s$: 20.1 $nC/cm^2$, switching time: 150 $\mu$s, switching angle: 60.3°.

Test mixture 5
15.0% by wt. of 4-(2-heptylimidazo[2,1-b]thiazol-6-yl) phenyl nonanecarboxylate;
85.0% by wt. of BM;
Phase sequence [°C]:
I - 78.7 - N* - 73.6 - $S_A$ - 68.2 - $S_C$* - ;
$P_s$: 20.5 $nC/cm^2$, switching time: 140 $\mu$s, switching angle: 56.2°.

Test mixture 6
15.0% by wt. of 4-octyloxyphenyl 2-heptylimidazo[2,1-b]-thiazole-6-carboxylate;
85.0% by wt. of BM;
Phase sequence [°C]:
I - 78.2 - N* - 71.5 - $S_A$ - 61.3 - $S_C$* - ;
$P_s$: 16.3 $nC/cm^2$.

What is claimed is:
1. An imidazothiazole derivative of the formula

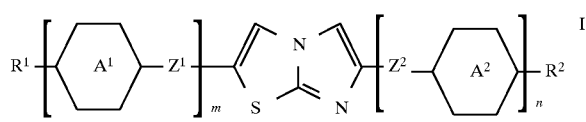

in which the symbols m, n, $R^1$ and $R^2$ have the following meanings:

m and n are 0 or 1, with the proviso that m+n=1 or 2
$R^1$ is $R^3$ or $Q^1$ or, if n is 0 and m is 1, also $R^3$-$A^3$-$Z^3$-,
$R^2$ is $R^4$ or $Q^2$ or, if n is 1 and m is 0, also $R^4$-$A^4$-$Z^4$,
and, independently of one another, $R^3$ and $R^4$ are each on alkenyl or alkenyl radical incorporating at least three carbon atoms in which one methylene group or a plurality of non-neighboring methylene groups are optionally replaced by —O—, —COO— or —OOC—, and/or one hydrogen atom or a plurality of hydrogen atoms are replaced by fluorine or chlorine, $Q^1$ and $Q^2$ are each one of the following chiral groups

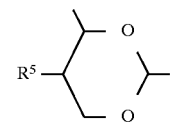

i

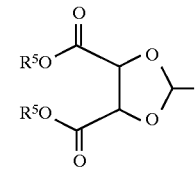

ii

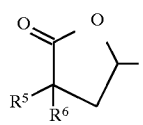

iii

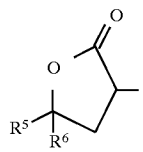

iv

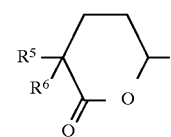

v

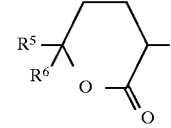

vi

-continued

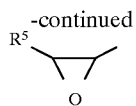

vii in which $R^5$ and $R^6$ are each an alkyl or alkenyl radical in which one methylene group or a plurality of non-neighbouring methylene groups may be replaced by —O—, —COO— or —OOC—, and/or one hydrogen atom or a plurality of hydrogen atoms may be replaced by fluorine or chlorine, with the proviso that the oxygen atoms are not linked directly to the ring in $Q^1$ or $Q^2$, $A^1$, $A^2$, $A^3$ and $A^4$ are trans-1,4-cyclohexylene or are 1,4-phenylene which is unsubstituted or monosubstituted or disubstituted by fluorine, chlorine, cyano or methyl, and $Z^1$, $Z^2$, $Z^3$ and $Z^4$ are each a single bond, —CH$_2$—CH$_2$—, —O—CH$_2$—, —CH$_2$—O—, —COO—, —OOC—, —C≡C—, —(CH$_2$)$_4$—, —O(CH$_2$)$_3$—, —CH=CH—CH$_2$O—, —OCH$_2$—CH=CH—, —CH=CH—(CH$_2$)$_2$— or —(CH$_2$)$_2$—CH=CH—.

2. An imidazothiazole derivative as claimed in claim 1, which is optically inactive and forms a tilted smectic phase.

3. An imidazothiazole derivative as claimed in claim 1, which is optically active.

4. An imidazothiazole derivative as claimed in claim 1, wherein the radicals $R^3$, $R^4$, $R^5$ and $R^6$ are straight-chain or branched and each have 3 to 12 carbon atoms.

5. An imidazothiazole derivative as claimed in claim 1, wherein $A^1$ and/or $A^2$ are 1,4-phenylene, 2-fluoro-1,4-phenylene, 3-fluoro-1,4-phenylene or 2,3-difluoro-1,4-phenylene.

6. An imidazothiazole derivative as claimed in claim 1, wherein at least one of $Q^1$s and $Q^2$ is of one of the formula i and the formula ii.

7.

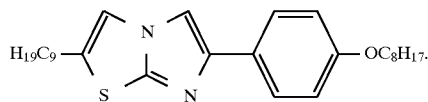

8. A liquid crystalline mixture having at least two components, comprising a content of at least one imidazothiazole derivative of the formula

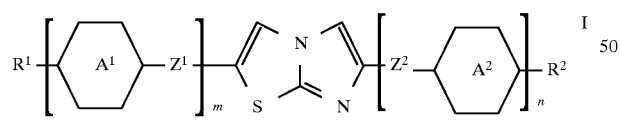

in which the symbols m, n, $R^1$ and $R^2$ have the following meanings:

m and n are 0 or 1, $R^1$ is $R^3$ or $Q^1$ or, if n is 0 and m is 1, also $R^3$-$A^3$-$Z^3$-, $R^2$ is $R^4$ or $Q^2$ or, if n is 1 and m is 0, also $R^4$-$A^4$-$Z^4$-, and, independently of one another, $R^3$ and $R^4$ are each an alkyl or alkenyl radical in which one methylene group or a plurality of non-neighbouring methylene groups are optionally replaced by —O—, —COO— or —OOC—, and/or one hydrogen atom or a plurality of hydrogen atoms are replaced by fluorine or chlorine, $Q^1$ and $Q^2$ are each one of the following chiral groups

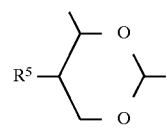
i

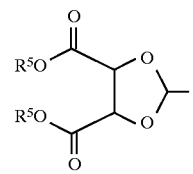
ii

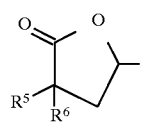
iii

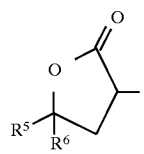
iv

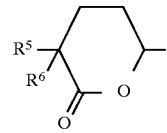
v

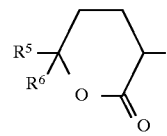
vi

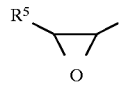
vii in which $R^5$ and $R^6$ are each an alkyl or alkenyl radical in which one methylene group or a plurality of non-neighbouring methylene groups may be replaced by —O—, —COO— or —OOC—, and/or one hydrogen atom or a plurality of hydrogen atoms may be replaced by fluorine or chlorine, with the proviso that the oxygen atoms are not linked directly to the ring in $Q^1$ or $Q^2$, $A^1$, $A^2$, $A^3$ and $A^4$ are trans-1,4-cyclohexylene or are 1,4-phenylene which is unsubstituted or monosubstituted or disubstituted by fluorine, chlorine, cyano or methyl, and $Z^1$, $Z^2$, $Z^3$ and $Z^4$ are each a single bond, —CH$_2$—CH$_2$—, —O—CH$_2$—, —CH$_2$—O—, —COO—, —OOC—, —C≡C—, —(CH$_2$)$_4$—, —O(CH$_2$)$_3$—,—CH=CH—CH$_2$O—, —OCH$_2$—CH=CH—, —CH=CH—(CH$_2$)$_2$— or —(CH$_2$)$_2$—CH=CH—.

9. A liquid crystalline mixture as claimed in claim 8, having at least one optically active dopant and a liquid crystalline material with at least one achiral component, wherein at least one of the one or more dopants are formed from a chiral imidazothiazole derivative of the formula I and the one or more components are formed from an achiral imidazothiazole derivative of the formula I.

10. A liquid crystalline mixture as claimed in claim 8, which contains at least one compound from the group consisting of compounds of the formulae

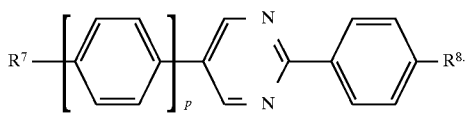
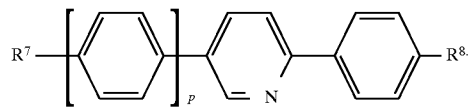

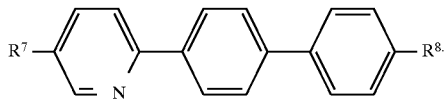
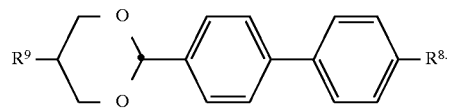

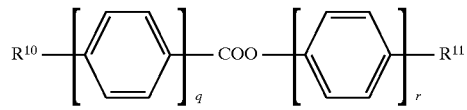

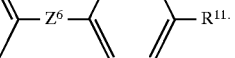

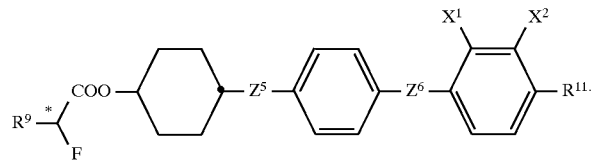

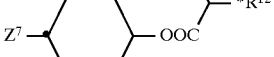

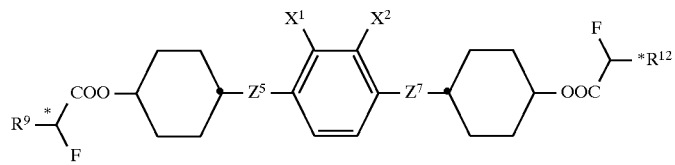

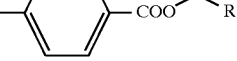

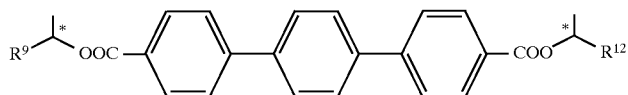

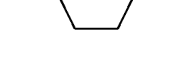

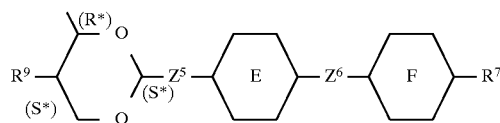

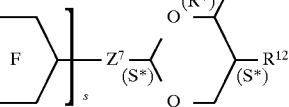

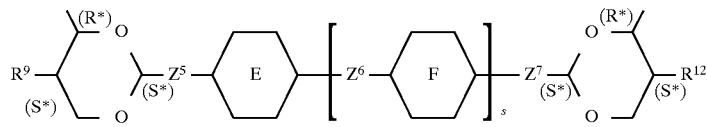

in which p is 0 or 1;

q and r are 1 or 2, q+r=2 or 3;

s is 0, 1 or 2;

$R^7$ and $R^8$, independently of one another, are alkyl, alkenyl, alkoxy, alkenyloxy, alkoxyalkyl, alkoxyalkoxy, alkanoyloxy, alkenoyloxy, alkoxycarbonyl, alkenyloxycarbonyl;

$R^9$ and $R^{12}$, independently of one another, are alkyl or alkenyl;

$R^{10}$ and $R^{11}$, independently of one another, are alkyl, alkenyl, alkoxy and/or alkenyloxy;

$Z^5$, $Z^6$ and $Z^7$, independently of one another, are a single bond, $CH_2-CH_2$ or $CH_2O$, and $Z^6$ is furthermore $OCH_2$, COO or OOC;

E and F, independently of one another, are phenylene-1,4-diyl or transcyclohexylene-1,4-diyl;

$X^1$ and $X^2$, independently of one another, are hydrogen or fluorine;

(R*) and (S*) denote the relative configurations.

11. An optical or electro optical apparatus containing at least one imidazothiazole derivative of the formula

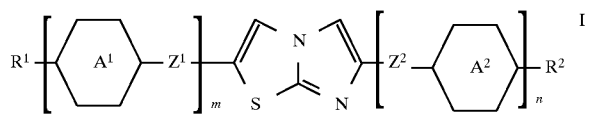

in which the symbols m, n, $R^1$ and $R^2$ have the following meanings:

m and n are 0 or 1, $R^1$ is $R^3$ or $Q^1$ or, if n is 0 and m is 1, also $R^3$-$A^3$-$Z^3$-, $R^2$ is $R^4$ or $Q^2$ or, if n is 1 and m is 0, also $R^4$-$A^4$-$Z^4$-, and, independently of one another, $R^3$ and $R^4$ are each an alkyl or alkenyl radical in which one methylene group or a plurality of non-neighbouring methylene groups are optionally replaced by —O—, —COO— or —OOC—, and/or one hydrogen atom or a plurality of hydrogen atoms are replaced by fluorine or chlorine, $Q^1$ and $Q^2$ are each one of the following chiral groups

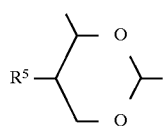 i

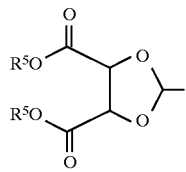 ii

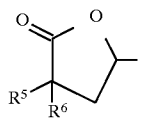 iii

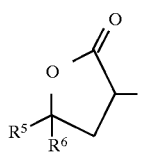 iv

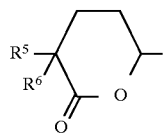 v

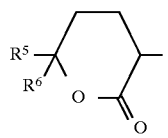 vi

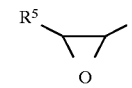 vii in which $R^5$ and $R^6$ are each an alkyl or alkenyl radical in which one methylene group or a plurality of non-neighbouring methylene groups may be replaced by —O—, —COO— or —OOC—, and/or one hydrogen atom or a plurality of hydrogen atoms may be replaced by fluorine or chlorine, with the proviso that the oxygen atoms are not linked directly to the ring in $Q^1$ or $Q^2$, $A^1$, $A^2$, $A^3$ and $A^4$ are trans-1,4-cyclohexylene or are 1,4-phenylene which is unsubstituted or monosubstituted or disubstituted by fluorine, chlorine, cyano or methyl, and $Z^1$, $Z^2$, $Z^3$ and $Z^4$ are each a single bond, —CH$_2$—CH$_2$—, —O—CH$_2$—, —CH$_2$—O—, —COO—, —OOC—, —C≡C—, —(CH$_2$)$_4$—, —O(CH$_2$)$_3$—,—CH=CH—CH$_2$O—, —OCH$_2$—CH=CH—, —CH=CH—(CH$_2$)$_2$— or —(CH$_2$)$_2$—CH=CH—.

12. An imidazothiazole derivative of the formula

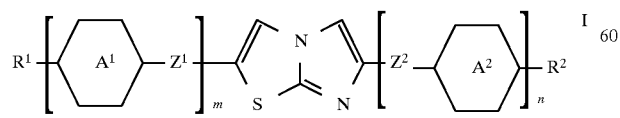 I which is optically active and in which the symbols m, n, $R^1$ and $R^2$ have the following meanings:

in which the symbols m, n, $R^1$ and $R^2$ have the following meanings:

m and n are 0 or 1, $R^1$ is $R^3$ or $Q^1$ or, if n is 0 and m is 1, also $R^3$-$A^3$-$Z^3$-, $R^2$ is $R^4$ or $Q^2$ or, if n is 1 and m is 0, also $R^4$—$A^4$—$Z^4$—, and, independently of one another, $R^3$ and $R^4$ are each an alkyl or alkenyl radical in which one methylene group or a plurality of non-neighbouring methylene groups are optionally replaced by —O—, —COO— or —OOC—, and/or one hydrogen atom or a plurality of hydrogen atoms are replaced by fluorine or chlorine, $Q^1$ and $Q^2$ are each one of the following chiral groups

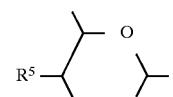 i

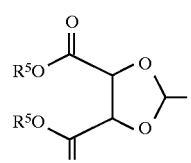 ii

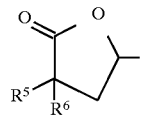 iii

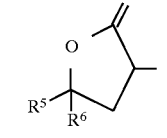 iv

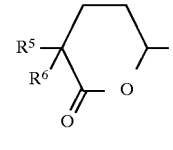 v

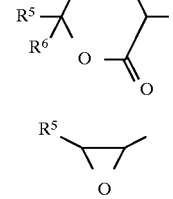 vi vii in which $R^5$ and $R^6$ are each an alkyl or alkenyl radical in which one methylene group or a plurality of non-neighbouring methylene groups may be replaced by —O—, —COO— or —OOC—, and/or one hydrogen atom or a plurality of hydrogen atoms may be replaced by fluorine or chlorine, with the proviso that the oxygen atoms are not linked directly to the ring in $Q^1$ or $Q^2$, $A^1$, $A^2$, $A^3$ and $A^4$ are trans-1,4-cyclohexylene or are 1,4-phenylene which is unsubstituted or monosubstituted or disubstituted by fluorine, chlorine, cyano or methyl, and $Z^1$, $Z^2$, $Z^3$ and $Z^4$ are each a single bond, —CH$_2$—CH$_2$—, —O—CH$_2$—, —CH$_2$—O—, —COO—, —OOC—, —C≡—C—, —(CH$_2$)$_4$—, —O(CH$_2$)$_3$—, —CH=CH—CH$_2$—O—, —OCH$_2$—CH=CH—, —CH=CH—(CH$_2$)$_2$— or —(CH$_2$)$_2$—CH=CH—.

13. An imidazothiazole derivative as claimed in claim 12, wherein the radicals $R^3$, $R^4$, $R^5$ and $R^6$ are straight-chain or branched and each have 3 to 12 carbon atoms.

14. An imidazothiazoles derivative as claimed in claim 12, wherein at least one of $A^1$ and $A^2$ is 1,4-phenylene, 2-fluoro-1,4-phenylene, 3-fluoro-1,4-phenylene or 2,3-difluoro-1,4-phenylene.

15. An imidazothiazole derivative as claimed in claim 12, wherein at least one of $Q^1$ and $Q^2$ is of the formulae i or ii.

* * * * *